(12) United States Patent
Goll et al.

(10) Patent No.: US 6,264,607 B1
(45) Date of Patent: Jul. 24, 2001

(54) TEST OBJECT GEOMETRY FOR ULTRASOUND TRANSMISSION CALIBRATION

(75) Inventors: Jeffrey Goll, Oswego, OR (US);
Donald Wood, San Jose, CA (US);
David Pratt, Tigard, OR (US)

(73) Assignee: Metra Biosystems, Inc., Mountain View, CA (US)

( * ) Notice: Subject to any disclaimer, the term of this patent is extended or adjusted under 35 U.S.C. 154(b) by 0 days.

(21) Appl. No.: 09/442,438

(22) Filed: Nov. 17, 1999

Related U.S. Application Data

(60) Provisional application No. 60/108,781, filed on Nov. 17, 1998.

(51) Int. Cl.[7] .................................................. A61B 8/00
(52) U.S. Cl. ........................................... 600/437; 600/438
(58) Field of Search ................................. 600/437, 438, 600/444, 443, 447

(56) References Cited

U.S. PATENT DOCUMENTS

| | | | |
|---|---|---|---|
| 4,181,004 | 1/1980 | Dominy et al. | 73/1 DV |
| 4,558,585 | 12/1985 | Berry, Jr. | 73/1 DV |
| 5,755,228 | 5/1998 | Wilson et al. | 128/660.06 |
| 5,807,250 | * 9/1998 | Ohtomo et al. | 600/437 |
| 5,931,780 | * 8/1999 | Giger et al. | 600/437 |
| 5,944,665 | * 8/1999 | Iino et al. | 600/437 |

FOREIGN PATENT DOCUMENTS

| | | |
|---|---|---|
| 0516353A1 | 12/1992 | (EP) . |
| 0765635A3 | 4/1997 | (EP) . |
| WO98/12966 | 4/1998 | (WO) . |

OTHER PUBLICATIONS

McCarthy, K., "Quality Assurance in Medical Imaging" from a meetin gof the Instrument Science and Technology Group of the Institute of Physics on 'Quality Assurance Aspects of Medical Imaging', *IOP Short Meeting Series No. 2 Institute of Physics*, London, pp. 77–80, Jun., 1986.

* cited by examiner

*Primary Examiner*—Marvin M. Lateef
*Assistant Examiner*—Maulin Patel
(74) *Attorney, Agent, or Firm*—Bromberg & Sunstein LLP

(57) ABSTRACT

A cylindrical test object for use in calibrating an ultrasonic bone analyzer has opposing ends that each contain a transducer seat optimized to allow intimate acoustic contact in spite of mechanical errors such as might be encountered in a scanning system. The test object is made of material having known ultrasonic characteristics. When opposing transducers are placed in the test object transducer seats, the test object is lifted off the holder and is free to rotate and translate over sufficient range to compensate for variances in the relative positions of the transducers. The shapes of the transducer ends and transducer seats are chosen to allow intimate acoustic contact in spite of any such translation or rotation. The test object may be a solid or a liquid encased in a solid.

27 Claims, 5 Drawing Sheets

TEST OBJECT GEOMETRY FOR ULTRASOUND TRANSMISSION CALIBRATION

This application claims priority from U.S. provisional patent application No. 60/108,781, filed Nov. 17, 1998, the contents of which are hereby incorporated herein by reference.

TECHNICAL FIELD

The present invention relates to a system for the acoustic analysis of bone, and more particularly to a test object for calibrating such a system for accuracy and uniformity.

BACKGROUND ART

Various methods are known for measuring bone characteristics using acoustic techniques to identify patients in need of treatment for bone conditions and diseases. Many acoustic techniques utilize a first transmitting transducer to provide an acoustic signal, typically at ultrasonic frequencies, to the subject from a first external location and a second receiving transducer at a second external location disposed on the opposite side of the bone of interest to receive the signal transmitted by the first transducer through the bone and intervening soft tissue. Typically, such transducers are coupled to the subject through a suitable fluid, such as water or through ultrasound transmission gel.

One acoustic measure of bone often used is the so-called Broadband Ultrasound Attenuation (BUA), typically quoted for the frequency range of approximately 200 to 600 kHz. The BUA is defined as the slope of a linear logarithmic-amplitude versus frequency plot of the energy transmitted through the heel. BUA measures are typically performed by Fourier transforming the signal produced in the receiving transducer due to transmission of a broadband acoustic pulse through the bone undergoing measurement. The Fourier components of the received signal are typically ratioed to the corresponding components measured through a medium of known spectral attenuation characteristics so that the slope of the bone attenuation versus frequency may be derived.

Trabecular bone is known to have the effect of preferentially attenuating higher frequencies—the extent of the preferential attenuation is known to decrease as the bone becomes increasingly porous. Thus, the BUA similarly decreases for more porous bone. BUA measurements are complicated by a variety of factors. For example, the BUA computed may depend not only on the apparatus used, but on the length and portion of the time domain record that is used, the type, if any, of window function used with the data, the frequency range and method used for estimation of the slope, and the methods used for calibration. Further difficulties may result from the presence of received signals that result from transmission through the bone via multiple paths.

The early portion of the received waveform may be more representative of the measured body part. It is desirable, moreover, to express the results of measurements made with respect to early or other transient portions of the received signal in terms of BUA, since it has been common practice to relate BUA values to bone condition empirically.

For clinical utility, measured and quoted characteristics must be highly reproducible from measurement to measurement for a given subject, whether the measurements are made with one, or more than one, measurement unit. In order to monitor the reliability and repeatability of the measurements, standards of various sorts have been provided to simulate the attenuation properties of bone, namely preferential attenuation of higher frequencies. One type of standard requires fabrication of a model heel structure, or phantom, such as an epoxy-resin matrix filled with a fluid, or an epoxy resin filled with particles of another material such as tungsten powder or glass beads. Another type of standard known in the art is an electronic standard that simulates the spectral effect of an attenuating bone.

SUMMARY OF THE INVENTION

One embodiment of the present invention includes a calibration device for a bone density analyzer having substantially opposing ultrasonic transducers with spherical section ends. The calibration device includes a test object having opposing ends, the test object being made of material having known acoustic characteristics; and a transducer seat in each opposing end that receives the transducers, each transducer seat having a spherical section shape corresponding to the spherical section ends of the transducers that allows free translational and rotational coupling of the seat with a transducer.

A further embodiment may include a test object holder having a cradle that supports the test object. An elastomeric o-ring may be around the outer surface to stabilize the test object when laying at rest in the cradle. In such an embodiment, a lanyard assembly may connect the test object and the test object holder without affecting the acoustic characteristics of the test object.

The test object may have a cylindrical shape and/or be made of ABS plastic. The bone density analyzer may be of the mechanical scanning type. Each transducer seat may have an inner radius of curvature that creates an area of the transducer seat that matches the shape of a transducer end, and an outer radius of curvature that extends the area of direct acoustic contact between the transducer end and the transducer seat, and that limits any suction force between the transducer and the transducer seat.

Any of the above embodiments may also be used in a calibration device for a bone density analyzer that includes a test object having opposing ends connected by walls that define a fluid filled cavity, the fluid having known acoustic characteristics; and a transducer seat in each opposing end that receives the spherical section ends of the transducers. Each transducer seat may have an opening having a radius of curvature approximating the cross-sectional curvature of the transducer sidewall, and an inner elastomeric sheet that seals the fluid cavity and that may deform to accommodate the shape of a transducer end. The inner elastomeric sheet may be made of latex rubber or silicone rubber. Each transducer seat may have a shape such that when a spherical section end of a transducer contacts the seat for a calibration measurement, the contact area is substantially equivalent to the contact area when a spherical section end of a transducer contacts a human foot during normal use of the bone density analyzer. The fluid may be water or a mixture of fluids such as a solution of water and alcohol.

BRIEF DESCRIPTION OF THE DRAWINGS

The present invention will be more readily understood by reference to the following detailed description taken with the accompanying drawings, in which.

DETAILED DESCRIPTION OF SPECIFIC EMBODIMENTS

A preferred embodiment of the present invention includes a test object for calibrating an ultrasonic bone density measuring system such as that described in U.S. Pat. No. 5,720,290 ("the Bubler patent"), the specification for which is hereby incorporated herein by reference. Such calibrating is performed, for example, in accordance with a special calibration procedure such as that described U.S. Pat. No. 5,947,902, issued Sep. 7, 1999, which in turn was a continuation-in-part of U.S. application Ser. No. 08/938,101, filed Sep. 26, 1997, claiming priority from U.S. provisional application No. 60/026,815, filed Sep. 27, 1996, all of which are herein incorporated by reference.

The Bubler patent describes acoustic procedures that take advantage of the fact that relatively nonporous and connective bone, on the one hand, and relatively porous and non-connective bone, on the other hand, respond differently to ultrasound acoustic inputs. Analysis of the acoustic signal provides one or more numerical measures related to bone condition and referred to as "Ultrasonic Bone Indices" (UBIs). Different UBIs, which may be identified by a numerical suffix, for example, UBI-2, UBI-3, etc. are described in the Buhler patent and the aforementioned applications. In connection with the general signal processing techniques utilized (but not their specific utilization in the context of ultrasonic bone testing), the following references are pertinent: Boualem Boashash, ed., Time-Frequency Signal Analysis (Wiley, 1992) (especially pertinent to instantaneous frequency analysis; see especially ch. 2, pages 43–73) and Richard Shiavi, Introduction to Applied Statistical Signal Analysis (Irwin, 1991) (especially pertinent to Burg Spectral Estimation; see especially pages 369–373). These texts are hereby incorporated herein by reference.

Figure 1:
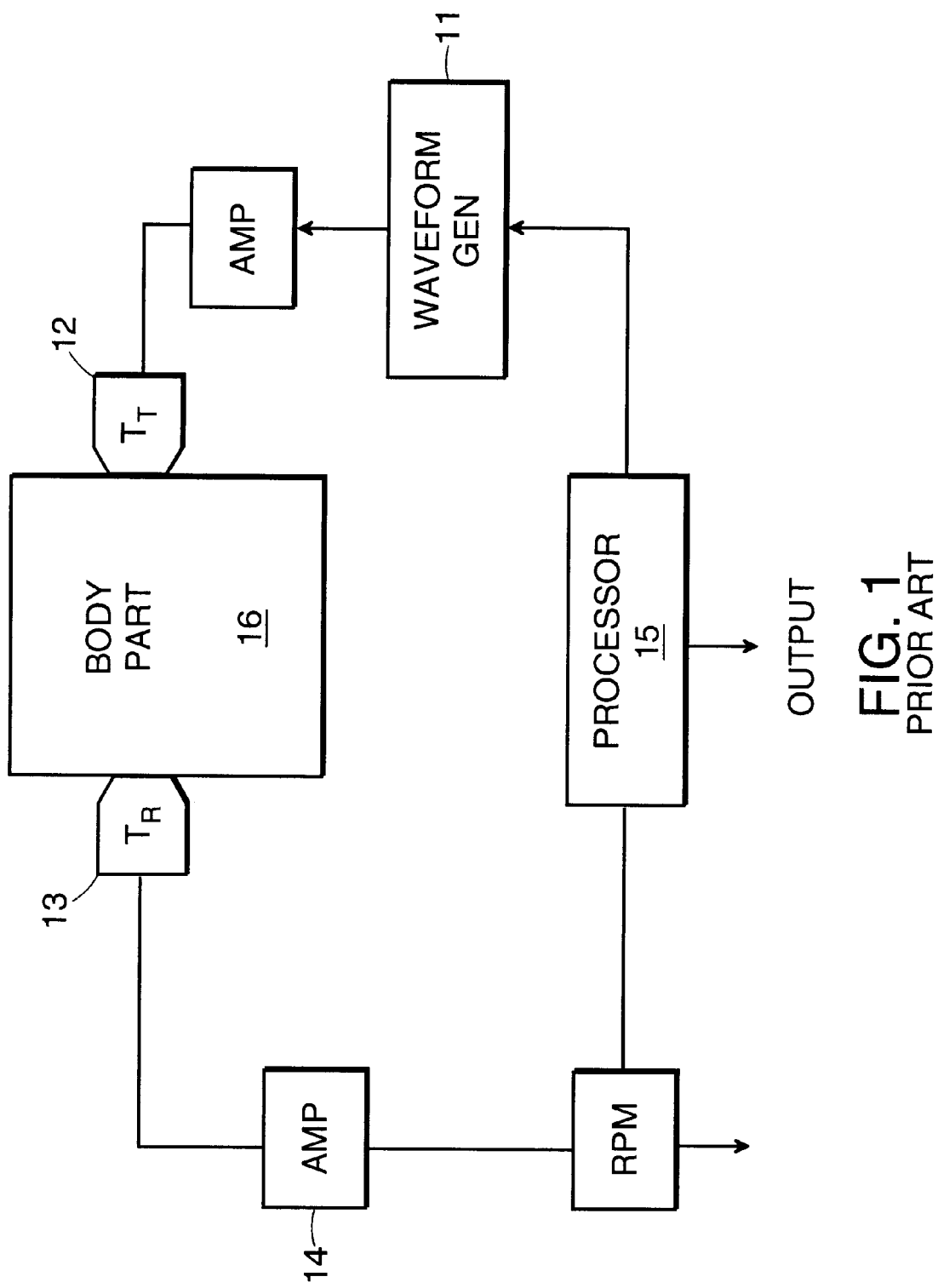
FIG. 1 is a diagram showing the general components of a system that measures a body part using ultrasound, and that is calibrated using a test object according to a preferred embodiment of the present invention.

FIG. 1 illustrates the general configuration of such an ultrasound bone density measuring system. An ultrasonic excitation waveform is generated by waveform generator 11, and delivered to transmitting transducer 12 (TT). Transmitting transducer 12 is acoustically coupled to body part 16 of a subject and produces an acoustic wave that is propagated into body part 16, and in particular into bone therein. The receiving transducer 13 (TR), is also acoustically coupled to body part 16 and receives a signal resulting from the effects, among other things, of propagation of the ultrasonic acoustic wave through the bone and the body part. Components for transmitting and receiving an acoustic signal via a body part are collectively known as an "acoustic transceiver." The output of the receiving transducer 13 is amplified by amplifier 14 and processed by processor 15 which analyzes the signal, makes a determination reflective of the condition of the bone, and provides an output.

Figure 2:
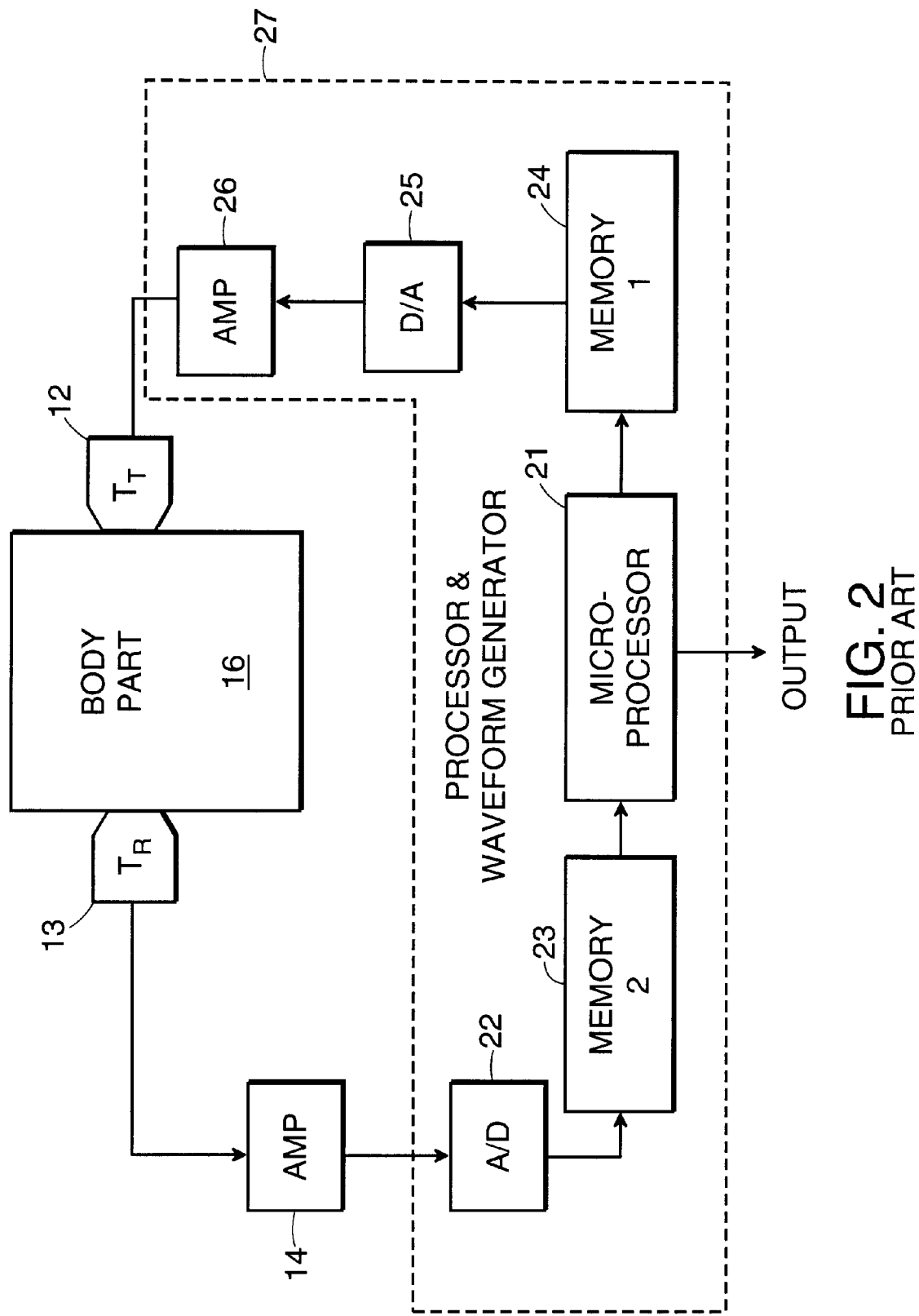
FIG. 2 is a diagram showing a digital implementation of the system of FIG. 1.

While the elements of FIG. 1 may be implemented in analog components, in a manner known in the art, it is convenient to use a digital implementation such as that shown in FIG. 2. The body part 16 may be, for example, the region proximate to the calcaneus in the heel of a subject. FIG. 2 shows processor 15 and waveform generator 11 being realized in a unit 27 which includes a microprocessor 21 that controls both processing of the output from the receiving transducer 13 and the generation of the waveform used for exciting the transmitting transducer 12. This exciting waveform is stored in digitized form in memory 1, item 24, and under control of microprocessor 21 is run through digital-to-analog converter 25 before being provided to amplifier 26 and the transmitting transducer 12. Similarly, the output of receiving transducer 13 is fed from amplifier 14 to analog-to-digital converter 22 and this digitized output is stored in memory 2, item 23. The stored output is then processed by microprocessor 21, which provides a data output indicating the condition of the bone.

It is important that such bone density measurement systems produce analysis results that are as accurate as possible and uniformly consistent from one machine to another. Accuracy and consistency may be affected in part by operator-related variations. Such operator-related variations may be addressed by careful and effective operator training. Accuracy and consistency are also affected by tolerance-related variations due to slight structural differences in individual analyzer systems and similar variations in the electrical characteristics of system components. Such tolerance-related variations may be addressed in system design and by calibration devices and techniques.

Of course, it is not possible to provide each bone density measurement unit with a reference human foot to be used for system calibration. It is practical, however, to use a special standard calibration test cell or test object (also known in some cases as a phantom) having known acoustic characteristics. These characteristics may be, but are not required to be similar to those of a human foot. In such a test object, the acoustic characteristics of interest would be a function of the material medium of the device and its geometry. Advantageous features of a test object medium used for the system response calibration measurements in some quantitative ultrasound systems may include:

1) Acoustic propagation of the test object medium in the frequency range of interest should be nearly neutral. Any frequency dependence of the acoustic attenuation or speed of sound in the medium should be minimal so that the medium simply passes the vibration created by the transmitter to the receiver with little or no change other than in the overall power level.

2) Acoustic coupling into and out of the test object medium should substantially replicate any effects associated with the acoustic coupling into and out of a human subject's foot.

3) Coupling into and out of the test object should be easily and repeatably achieved.

Any deviations in the first two requirements demands compensation by the mathematical or physical techniques used for calibration.

It is natural to consider making such measurements with a test object having a fluid medium such as water, which generally meets the above requirements to an excellent approximation. However, a test object made of a solid material would be much more convenient to use. Use of a solid material test object, however, imposes substantial additional challenges of its own. This is particularly the case for a quantitative ultrasound system that uses mechanical scanning, especially when the transducer or other surface designed to contact the test object is curved. The following factors must be considered:

1) The physical locations of the transducers when the calibrating measurement is taken are likely to vary somewhat from time to time and, especially, from machine to machine. This is especially likely in mechanical scanning systems, in which the transducers generally are driven to the measurement site using motors. Accordingly, the test object must be able to tolerate variations in the precise measurement location.

2) The orientation (rotation angle) of the transducers may vary somewhat from machine to machine or even from time to time. Accordingly, the test object must be able to tolerate small variations in the orientation of the transducers.

3) While flat-faced transducers may provide the easiest shape with which to make the calibration measurement of a solid test object, such flat-faced transducers may not be well adapted to measuring the feet of human subjects.

4) If the transducers, the test object, or both are hard solid objects, the pressure that is required to be applied to the transducers to optimize a calibration or verification measurement may exceed the pressure that is comfortable or desirable for a human subject measurement.

Various shapes may be used provided the various requirements described herein are met. In a preferred embodiment, a cylindrical plastic plug is used as a test object. In accordance with preferred embodiments of the invention, a cylindrical test object should preferably embody the following features:

1) The length of the test object should be within the range of human heels in the general vicinity of and below the ankle.

2) The width of the test object should be great enough that any acoustic reflections off the side of the test object are delayed sufficiently to avoid interfering with the calibration calculations. Alternatively measures can be taken to minimize the magnitude of any reflections off the side of the test object.

3) The test object material should be substantially acoustically neutral with little frequency-dependent attenuation, little velocity dispersion, and minimal distortion due to transfer of acoustic energy between the transducers and the test object.

4) Transducer seats should be fashioned in opposing walls of the test object that optimize the acoustic coupling (which may be aided by an ultrasonic transmission gel), between the transducer and the test object.

5) The test object should be mounted in such a way that there is translational and rotational freedom to accommodate variations in mechanical structure that might lead to imprecision in the location or orientation of the transducers at the time of the calibration measurement.

6) To assure reliable and reproducible acoustic contact between the test object and the transducers, appropriate magnitude pressure needs to push the transducers against their respective seats.

7) Mechanical scanning motors should be able to easily remove the transducers from the contact area on the test object.

Various embodiments of the present invention have features that may be applicable more generally, but that are specifically appropriate for a scanning ultrasonic analyzer that mechanically scans the transducers and for which the transducers contact the body part through a layer of gel. The performance of the calibration measurement in such a system may be more difficult than for a system that uses fixed location transducers or a water bath. For example, in a scanning system the transducers typically must move to the location at which the calibration measurement is made. As compared with a non-scanning system in which the transducers may be optimally placed at a single location, a scanning system may suffer from small additional errors. In particular, when the transducers move to the desired measurement site there may be small errors in location for one or both transducers. There may also be small axial rotational errors for one or both transducers. Therefore it is preferred that a scanning system be designed so that these small positional and rotational errors lead to minimal errors in the final measurements. In particular it is desirable that the design gives accurate, repeatable calibration, which in turn requires that the variations in the contacts between the test object and the transducers are minimized, or that calibration measurement results be tolerant of small contact variations, or both.

Figure 3B:
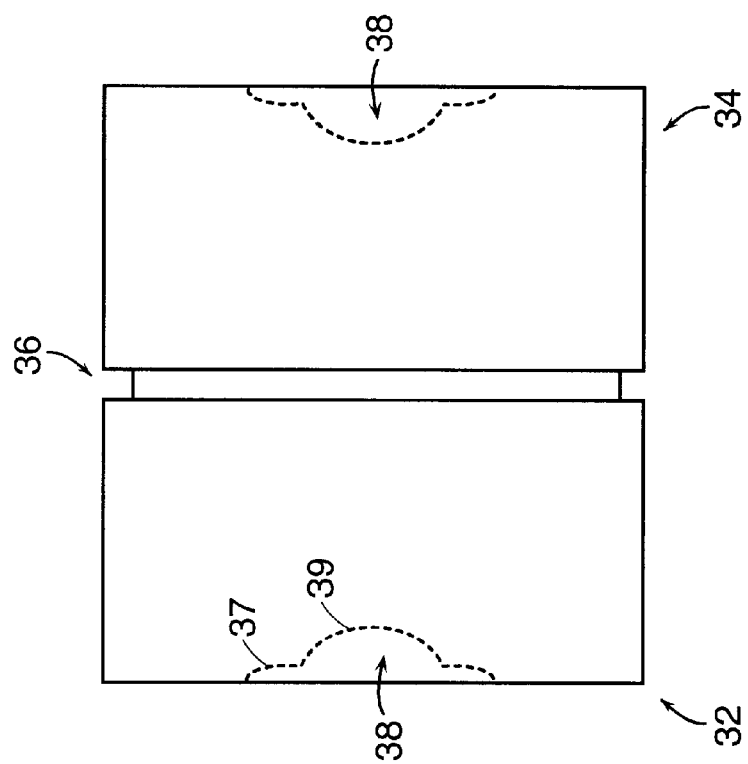
FIG. 3 shows side and top views of a solid cylindrical test object according to a preferred embodiment.
Figure 3A:
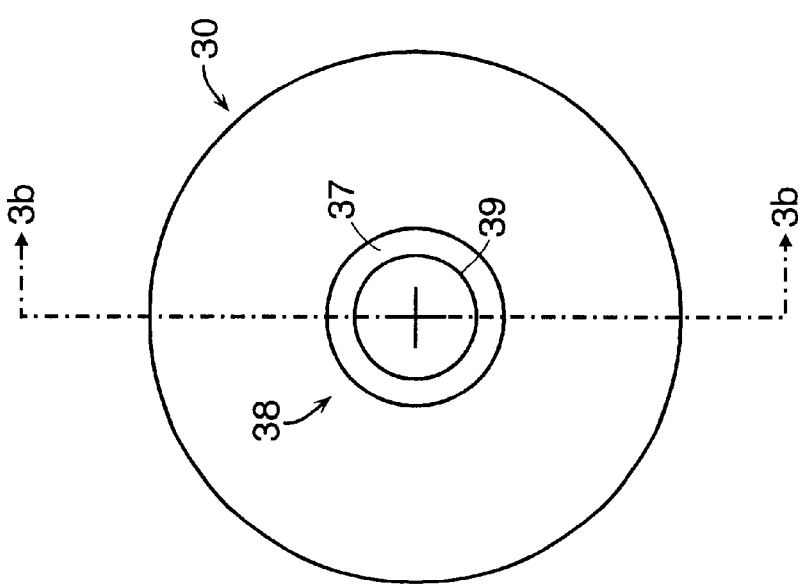

A preferred embodiment based on the above criteria uses a cylindrical test object as shown in FIG. 3. The test object 30 has opposing ends 32 and 34 having a substantially circular cross-section. Each opposing end has a transducer seat 38 with two spherical section curvatures, a wider outer curvature 37 and a deeper inner curvature 39. The inner curvature 39 of each transducer seat 38 has a substantially spherical section curvature that is adapted for receiving piezoelectric ultrasound transducers 12 and 13, which in turn have ends shaped as substantially spherical sections complementary to the inner curvature 39, and have a hard plastic covering with about a 1 mm extent in front of the active element. The wider outer section 37 of each transducer seat 38 has a curvature somewhat larger than that of the inner section. A test object o-ring groove 36 is located at the center of the cylinder length.

Figure 4A:
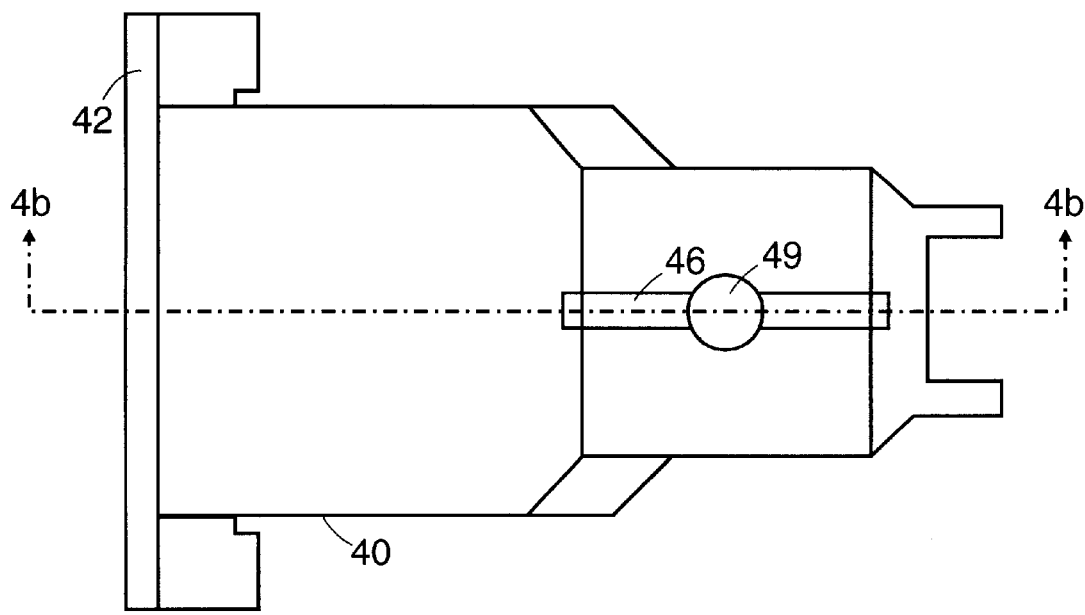
FIG. 4 shows top and side views of a holder for the test object of FIG. 3.
Figure 4B:
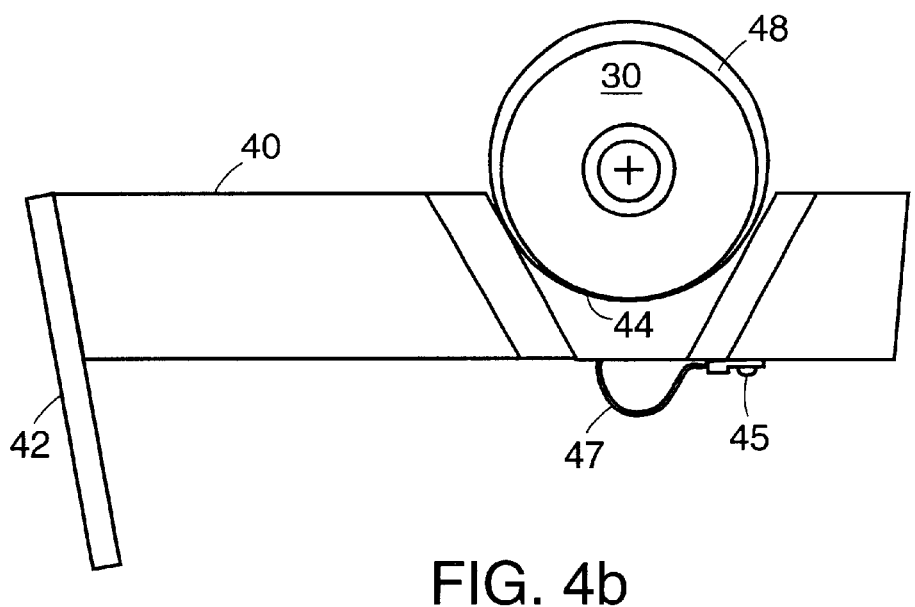

FIG. 4 shows a test object holder 40 having a positioning bracket 42. The test object holder 40 has a test object cradle 44 to properly hold the cylindrical test object 30 for calibration measurements. In a preferred embodiment, the cradle 44 is in the form of a partial cylindrical bore through the test object holder. For example, if the test object diameter is nominally 1.745 inches in diameter, the cradle 44 may be formed by a holder bore through of a 2.050 inch diameter circle of 60 degrees on either side of perpendicular. Centered in the cradle 44, is an o-ring groove 46, typically about 0.25 inches deep.

The test object o-ring 48 rests in the test object o-ring groove 36 so that the o-ring 48 also nestles in the cradle o-ring groove 46 when the test object 30 is supported in the test object cradle 44. This o-ring arrangement serves to prevent the test object 30 from sliding around in the cradle 44. A preferred embodiment may also include a lanyard hole 49 in the center of the cradle o-ring groove 46 through which a lanyard 47 may be fed that secures the o-ring 48 to the test object holder 40 with a connecting rivet 45 in order to limit how far the test object 30 may separate from the test object holder 40. The lanyard 47 may be looped around the o-ring 48 to complete the attachment A preferred embodiment uses a test object 30 made of ABS plastic. Although ABS plastic is well-suited for such an application, it is not ideal, having some frequency dependence and some effects due to the role of shear acoustic modes that play a very different role in a human foot than in plastic. These imperfections may be accounted for in the calibrating procedure. ABS plastic also enjoys other secondary characteristics including high toughness, rigidity and impact strength; abrasion resistance; moisture and creep resistance; and easy thermoforming with excellent mold detail. A test object 30 having a length of 4–5 cm has been found to work satisfactorily and be well within the range of widths of human heels. A test object 30 having a width of 4 cm or greater is sufficient to assure that any acoustic reflections off the sidewalls are delayed by at least 6 microseconds, long enough to avoid interfering with the calibration measurements.

Transducer seats 38, in a preferred embodiment, are of complementary shape to the transducer housing. Specifically, the transducer housing is a spherical section near the contact surface and the preferred contact area of the transducer seat 38 in the test object 30 is a complementary spherical section. In practice, this complementary section needs only to cover the bottom few millimeters of the transducer seat 38. If the section is too deep, large suctions forces may be set up that make it difficult for the transducer motors to exit the contact area of the transducer seat 38 after the calibration measurement. In a preferred embodiment, the transducer seat 38 has two radii of curvature—a larger radius for the outer section 37, and a smaller radius at the deeper bottom part of the contact area, inner curvature 39 that matches the transducer tip radius. The larger curvature outer section 37 extends the area of intimate acoustic contact without generating excessive suction forces. In addition, it provides a larger target for the transducer 12 or 13 when it drives to the measurement location. Thus, larger errors in the transducer position are accommodated by this arrangement.

Several features of a preferred embodiment combine to satisfy the requirement that the test object 30 have translational and rotational freedom to accommodate variations in mechanical structure. That is, the arrangement of the test object 30 and the test object holder 40 allows the system transducers 12 and 13 to engage the contact area of the transducer seats 38 of the test object 30 even if one or both of the transducers 12 and 13 are several mm from their nominal location.

In addition, the test object 30 may be lifted free and clear of the test object cradle 44 by several mm at the time the measurement is performed so that it is free to translate or rotate without mechanical constraint. This arrangement accommodates the offset of errors of several mm in any direction. The spherical section shape of the transducers 12 and 13 and the transducer seats 38 further allows intimate acoustic contact in spite of potential errors in the rotational orientation of the transducers 12 and 13 when they enter the transducer seats 38. After the measurement is completed, the transducer motors return the test object 30 to the rest position on the cradle 44. The o-ring arrangement provides a means of mounting the test object 30 on the test object holder 40 in way that prevents the test object 30 from sliding away from its rest position on the test object cradle 44. Furthermore, tethering the test object 30 to the test object holder 40 accommodates the required freedom of motion while resisting complete separation of the two. Such a test object tether 47 must contribute minimal or zero distortions to the calibration measurement of the test object 30 since a tether attaching assembly that uses a deep hole may cause acoustic reflections that undesirably distort the calibration test results. In a preferred embodiment, the tether 47 is looped around the o-ring 48 so that no hole needs to be made in the test object to facilitate attachment.

After the transducers 12 and 13 are driven to the approximate calibration test location with respect to the test object 30, and in the process lift the test object free and clear of the test object cradle 44, pressure is applied to push the transducers 12 and 13 into close acoustic contact with the test object 30 in the transducer seats 38. In this process, mechanical positioning errors are also accommodated. In a preferred embodiment, this may be achieved by allowing the operator to apply the pressure. In other embodiments, a mechanical system may be provided to apply a pressure that is generally somewhat greater than the pressure applied when measuring a foot.

The embodiment described may be subject to some difficulty associated with the differences between a solid plastic test object and a non-solid, non-plastic human foot. In a typical embodiment, these difficulties may be satisfactorily accommodated in the mathematics used for calibration. In addition, the difficulties may be further addressed by using a fluid reservoir within the test object instead of solid plastic. The fluid reservoir may be contained in a solid exterior. Contact is made using holes for the transducer ends through the solid exterior that are sealed using a thin layer of an acoustically near-transparent material such as latex or silicone rubber. The fluid needs to have known acoustic properties, and may be, for example, water or a solution of water and alcohol. With this arrangement, unlike with a solid test object, the acoustic load imposed on the transducer is more similar to that experienced when coupling to the soft tissue of a foot. Furthermore, since the acoustic path through the test object is nearly entirely through a fluid, shear modes are not transmitted. Again, this is unlike the situation with a solid test object, but is similar to the result of ultrasonic transmission through a human foot. By controlling the area of contact between the transducers and the test object transducer seats, it is possible to model physically the physical contact that is made between transducers and a foot in a typical measurement. For some transducer designs this contact area control is necessary to provide the most accurate model of the contact to a human foot. Thus, using a fluid reservoir within the test object may provide a more accurate model for use in calibration. This may simplify and make more accurate the results of the calibration technique.

Figure 5:
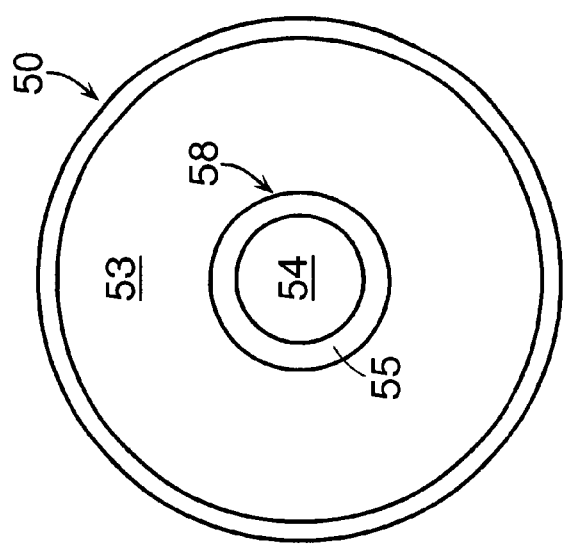
FIG. 5 shows side and top views of a fluid-filled cylindrical test object according to a preferred embodiment.
Figure 5:
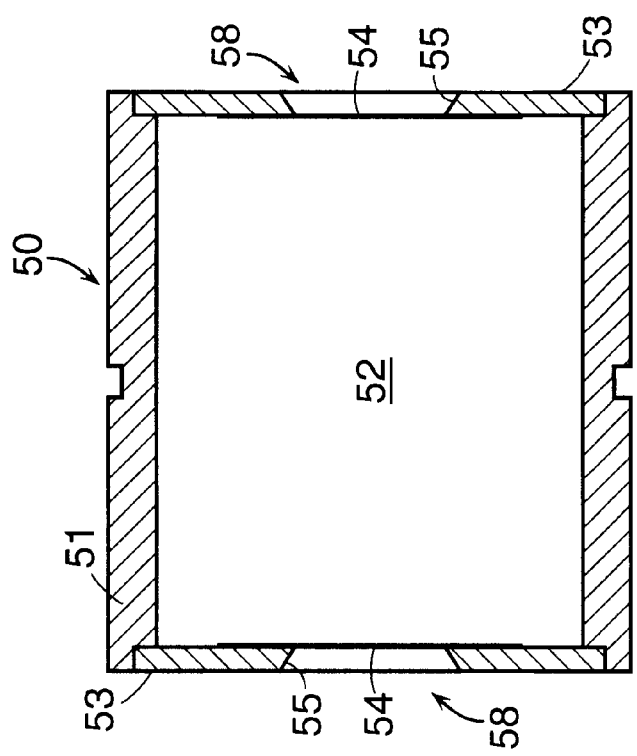

FIG. 5 shows top and side views of a fluid-filled cylindrical test object 50 according to a preferred embodiment. The test object 50 is hollowed out except for a thin wall 51 to define a fluid filled reservoir 52. Each transducer seat 58 is produced using an opening in the end face 53 that is sealed using a thin sheet of latex rubber, silicone rubber, or other suitable material to form a flat but flexible transducer seating surface 54. The opening sides 55 in the end faces may be chosen to have a spherical curvature. For example it may be advantageous to match, or nearly match, this curvature to the curvature of the transducer sidewall so as to improve the repeatability and precision of the contact between the transducer 12 and 13 and the transducer seat 58. The area over which intimate contact is made between the transducers 12 and 13 and the test object 50 is controlled by the size of the transducer seat area 54. The interior reservoir 52 may then be filled with water or other suitable fluid and sealed. The fluid-reservoir test object 50 illustrated in FIG. 5 may be used with the test object cradle 44 illustrated in FIG. 4 in the same manner as described in detail previously for the solid test object of FIG. 3.

What is claimed is:

1. A calibration device for a bone density analyzer having substantially opposing ultrasonic transducers with spherical section ends, the calibration device comprising:
   a test object having opposing ends, the test object being made of material having known acoustic characteristics; and
   a transducer seat in each opposing end that receives the transducers, each transducer seat having a spherical section shape corresponding to the spherical section ends of the transducers.

2. A calibration device according to claim 1, further comprising:
   a test object holder having a cradle that supports the test object when not in use and that allows the test object to be lifted free of the cradle when the transducers engage the transducer seats.

3. A calibration device according to claim 2, further comprising:
   an elastomeric o-ring around the outer surface of the test object that mechanically stabilizes the test object when the cradle supports the test object.

4. A calibration device according to claim 2, further including a lanyard assembly that connects the test object and the test object holder without affecting the acoustic characteristics of the test object.

5. A calibration device according to claim 1, wherein the test object has a cylindrical shape.

6. A calibration device according to claim 1, wherein the test object is made of ABS plastic.

7. A calibration device according to claim 1, wherein the bone density analyzer is of the mechanical scanning type.

8. A calibration device according to claim 1, wherein each transducer seat has:
   an inner radius of curvature that creates an area of the transducer seat that matches the shape of a transducer end, and
   an outer radius of curvature that extends the area of direct acoustic contact between the transducer end and the transducer seat, and that limits any suction force between the transducer and the transducer seat.

9. A calibration device for a bone density analyzer having substantially opposing ultrasonic transducers, the calibration device comprising:
   a test object having opposing ends, the test object being made of material having known acoustic characteristics; and
   a transducer seat in each opposing end that receives the transducers, each transducer seat having a shape that allows free translational and rotational coupling of the seat with a transducer.

10. A calibration device according to claim 9, further comprising:
   a test object holder having a cradle that supports the test object when not in use and that allows the test object to be lifted free of the cradle when the transducers engage the transducer seats.

11. A calibration device according to claim 10, further comprising:
   an elastomeric oaring around the outer surface of the test object that mechanically stabilizes the test object when the cradle supports the test object.

12. A calibration device according to claim 10, further including a lanyard assembly that connects the test object and the test object holder without affecting the acoustic characteristics of the test object.

13. A calibration device according to claim 9, wherein the test object has a cylindrical shape.

14. A calibration device according to claim 9, wherein the test object is made of ABS plastic.

15. A calibration device according to claim 9, wherein the bone density analyzer is of the mechanical scanning type.

16. A calibration device according to claim 1, wherein the test object opposing ends are connected by walls that define a fluid filled cavity, the fluid having known acoustic characteristics.

17. A calibration device according to claim 16, further comprising:
   a test object holder having a cradle that supports the test object when not in use and that allows the test object to be lifted free of the cradle when the transducers engage the transducer seats.

18. A calibration device according to claim 17, further comprising:
   an elastomeric o-ring around the outer surface of the test object that mechanically stabilizes the test object when the cradle supports the test object.

19. A calibration device according to claim 17, further including a lanyard assembly that connects the test object and the test object holder without affecting the acoustic characteristics of the test object.

20. A calibration device according to claim 16, wherein the test object has a cylindrical shape.

21. A calibration device according to claim 16, wherein the test object is made of ABS plastic.

22. A calibration device according to claim 16, wherein the bone density analyzer is of the mechanical scanning type.

23. A calibration device according to claim 16, wherein each transducer seat has:
   an opening having a radius of curvature approximating the curvature of the transducer sidewall, and
   an inner elastomeric sheet that may deform to accommodate the shape of a transducer end.

24. A calibration device according to claim 23, wherein the inner elastomeric sheet is one of latex rubber and silicone rubber.

25. A calibration device according to claim 16, wherein each transducer seat has a shape such that when a spherical section end of a transducer contacts the seat for a calibration measurement, the contact area is substantially equivalent to the contact area when a spherical section end of a transducer contacts a human foot during normal use of the bone density analyzer.

26. A calibration device according to claim 16, wherein the fluid is water.

27. A calibration device according to claim 16, wherein the fluid is a solution of water and alcohol.

* * * * *

UNITED STATES PATENT AND TRADEMARK OFFICE
CERTIFICATE OF CORRECTION

PATENT NO.     : 6,264,607 B1
DATED          : July 24, 2001
INVENTOR(S)    : Jeffrey Goll et al.

It is certified that error appears in the above-identified patent and that said Letters Patent is hereby corrected as shown below:

<u>Column 9,</u>
Line 43, replace "oaring" with -- o-ring --.

Signed and Sealed this

Twenty-fifth Day of March, 2003

JAMES E. ROGAN
*Director of the United States Patent and Trademark Office*